United States Patent [19]

Donald et al.

[11] Patent Number: 5,384,316
[45] Date of Patent: Jan. 24, 1995

[54] 4,16-DIAZATETRACYCLO[23.3.1.1.HU 14,17B .0 HU 4,9 TRIACONTA-16,19-DIENE-2,3,10-TRIONE DERIVATIVES

[75] Inventors: David K. Donald, Ashby-de-la-Zouch; Mark Furber, Kegworth, both of England

[73] Assignee: Fisons plc, Suffolk, England

[21] Appl. No.: 975,544

[22] PCT Filed: Aug. 14, 1991

[86] PCT No.: PCT/GB91/01384

§ 371 Date: Feb. 18, 1993

§ 102(e) Date: Feb. 18, 1993

[87] PCT Pub. No.: WO92/03441

PCT Pub. Date: Mar. 5, 1992

[30] Foreign Application Priority Data

Aug. 18, 1990 [GB] United Kingdom ............... 9018196
Feb. 2, 1991 [GB] United Kingdom ............... 9102305

[51] Int. Cl.⁶ ............ A61K 31/42; A61K 31/435; C07D 498/22
[52] U.S. Cl. .................... 514/183; 540/456
[58] Field of Search ................ 540/456; 514/183; 548/240, 241

[56] References Cited

U.S. PATENT DOCUMENTS 4,659,389  4/1987  Wumbles et al. ............. 106/279

FOREIGN PATENT DOCUMENTS 184162  6/1986  European Pat. Off. .
356399  2/1990  European Pat. Off. .
WO89/05304  6/1989  WIPO .

OTHER PUBLICATIONS

Jarrar et al, J. Heterocyclic Chem., 27, pp. 275–278 (1990).

*Primary Examiner*—Mukund J. Shah
*Assistant Examiner*—Philip I. Datlow
*Attorney, Agent, or Firm*—Nixon & Vanderhye

[57] ABSTRACT

Compounds of formula (I) are provided, wherein $R^1$ represents OH or $OCH_3$; $R^2$ represents OH or H; $R^3$ represents methyl, ethyl, propyl or allyl; X represents O, (H,OH) or (H,H); m represents 0 or 1; n represents 1 or 2; and pharmaceutically acceptable derivatives thereof; provided that when n is 1, then $R^3$ is allyl or propyl. The compounds are indicated inter alia as immunosuppresive agents.

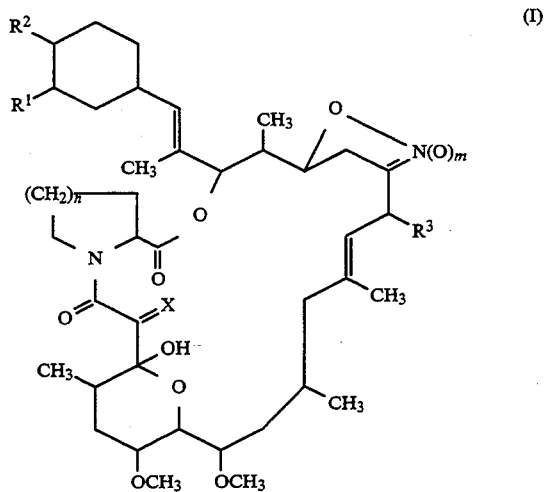

7 Claims, No Drawings

4,16-DIAZATETRACYCLO[23.3.1.1.HU 14,17B . 0 HU 4,9 TRIACONTA-16,19-DIENE-2,3,10-TRIONE DERIVATIVES

This invention relates to macrocyclic compounds, processes for their preparation, their use as medicaments, and compositions containing them.

European Patent Application 184162 (to Fujisawa Pharmaceuticals Co Ltd) discloses a number of macrocyclic compounds isolated from microorganisms belonging to the genus Streptomyces. The compounds are numbered FR-900506, FR-900520, FR-900523 and FR-900525, and the preparation of some of their derivatives is also described. The compounds are indicated as immunosuppressive agents.

International Patent Applications Nos WO 89/05304 and WO 91/02736 and European Patent Application No 413532 (to Fisons plc), European Patent Application 353678 (to Fujisawa Pharmaceuticals Co Ltd), European Patent Applications 349049, 349061, 358508 and 388153 (to Merck & Co Inc) and European Patent Application 356399 and International Patent Application WO 90/15805 (to Sandoz AG) also disclose a number of macrocyclic compounds whose indications include immunosuppressive activity.

We have now found a new group of macrocyclic compounds which possess advantageous properties over those disclosed previously.

According to the invention, there is provided a compound of formula I,

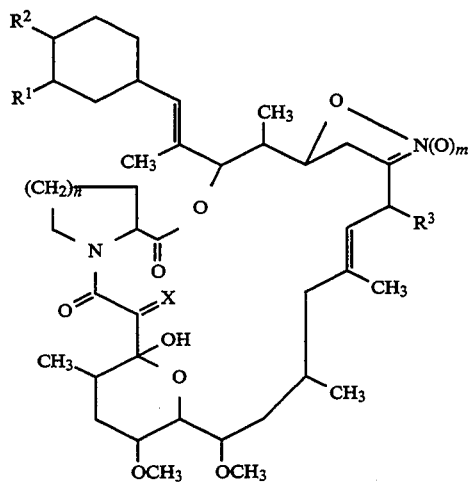

wherein
$R^1$ represents OH or $OCH_3$;
$R^2$ represents OH or H;
$R^3$ represents methyl, ethyl, propyl or allyl;
X represents O, (H,OH) or (H,H);
m represents 0 or 1;
n represents 1 or 2;
or a pharmaceutically acceptable derivative thereof; provided that when n is 1, then $R^3$ is allyl or propyl.

Compounds of formula I, and pharmaceutically acceptable derivatives thereof ("the compounds of the invention"), have the advantage that they are less toxic, are more efficacious, are longer acting, have a broader range of activity, are more potent, are more stable, produce fewer side effects, are more easily absorbed, are more soluble, or have other more useful physical or pharmacological properties, than compounds of the prior art.

Preferred groups of compounds are those in which: $R^1$ represents $OCH_3$; $R^2$ represents OH; X represents O; m represents 1; and n represents 2.

Pharmaceutically acceptable derivatives of compounds of formula I include prodrugs of compounds of formula I, i.e. compounds which may be metabolised in vivo to compounds of formula I. These include compounds which differ from compounds of formula I in that some or all of the OH groups (for example those which $R^1$ and $R^2$ may represent) are derivatized to esters or carbamates. Such esters may be prepared by conventional methods, for example reaction with a carboxylic acid and a coupling agent, or an acyl chloride. Such carbamates may also be prepared by conventional methods, for example reaction with an isocyanate. Specific esters and carbamates are $CH_3CO_2$—, $C_6H_5CO_2$—, $H_2NCO_2$— and $CH_3NHCO_2$—.

There is also provided a process for the production of a compound of the invention, which comprises cyclizing a compound of formula II,

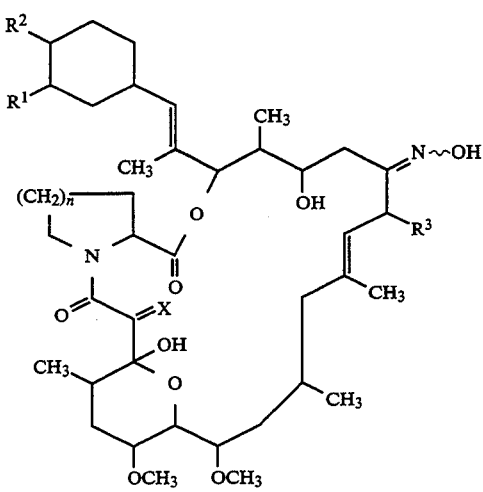

wherein $R^1$, $R^2$, $R^3$, X and n are as defined above, or a pharmaceutically acceptable derivative thereof; by the action of an appropriate oxidizing agent, and where necessary converting the resulting compound of formula I to a pharmaceutically acceptable derivative thereof.

Compounds of the invention in which m is 0 may be prepared from a corresponding compound of formula II by the action of Martin's sulfurane reagent, in a solvent which does not adversely affect the reaction (e.g. dichloromethane), below room temperature (e.g. from 0° to 10° C.). Martin's sulfurane reagent produces compounds of the invention having S-stereochemistry at C14 (i.e. the same stereochemistry as FR-900506) from Z-oximes of formula II, and compounds having R-stereochemistry at C14 from E-oximes of formula II.

Compounds of the invention in which m is 1 may be prepared from a corresponding compound of formula II by the action of lead tetraacetate, in a solvent which does not adversely affect the reaction (e.g. dichloromethane), at or around room temperature. Lead tetraacetate produces compounds of the invention having S-stereochemistry at C14 from both E- and Z-oximes of formula II. Compounds of the invention having R-stereochemistry at C14 in which m is 1 may be prepared from a corresponding compound in which m is 0 by oxidation, for example using a peracid such as perchlorobenzoic acid.

Compounds of formula II in which $R^2$ represents H may be prepared from a corresponding compound of formula II in which $R^2$ represents OH by converting the OH group into a leaving group [for example by reacting the compound of formula II with 1,1'-thiocarbonyldiimidazole to give an imidazol-1-yl(thiocarbonyl)oxy group], followed by substitution of the leaving group by hydrogen, for example by reaction with a hydride reducing agent such as tributyltin hydride in the presence of AIBN (2,2'-azobisisobutyronitrile).

Compounds of formula II in which X represents (H,H) may be prepared from a corresponding compound of formula II in which X represents O by selective reduction of the C2-carbonyl group. The reduction may be achieved by the action of $H_2S$, preferably in the presence of pyridine or an amine (for example morpholine), in a solvent which does not adversely affect the reaction (for example dimethylformamide, pyridine or methanol), at or around room temperature (see WO 91/02736).

Other compounds of formula II are either known or may be prepared using known techniques, for example those disclosed in WO 89/05304.

Where necessary, hydroxy groups in intermediate compounds may be protected using conventional protecting group chemistry [as described in "Protective Groups in Organic Chemistry", ed: J. W. F. McOmie, Plenum Press (1973) and "Protective Groups in Organic Synthesis", T. W. Greene, Wiley-Interscience (1981)]. A particularly useful protecting group is 'butyldimethylsilyl.

The compounds of the invention, may be isolated from their reaction mixtures using conventional techniques.

The teaching of all the documents mentioned above is herein incorporated by reference.

The compounds of the invention are useful because they possess pharmacological activity in animals: in particular they are useful because they possess immunosuppressive activity, e.g. as indicated in Tests A, B, C and D below.

Thus the compounds of the invention are indicated for use in the treatment or prevention of resistance to transplanted organs or tissues, such as kidney, heart, lung, bone marrow, skin, cornea, liver, medulla ossium, pancreas, intestinum tenue, limb, muscle, nervus, etc; and of autoimmune, inflammatory, proliferative and hyperproliferative diseases, and of cutaneous manifestations of immunologically-mediated diseases, for example rheumatoid arthritis, lupus erythematosus, systemic lupus erythematosus, Hashimoto's thyroiditis, multiple sclerosis, myasthenia gravis, type 1 diabetes, uveitis, nephrotic syndrome, psoriasis, atopical dermatitis, contact dermatitis and further eczematous dermatitides, seborrheic dermatitis, Lichen planus, Pemphigus, bullous Pemphigoid, Epidermolysis bullosa, urticaria, angiooedemas, vasculitides, erythemas, cutaneous eosinophilias, acne, Alopecia areata, eosinophilic fasciitis, atherosclerosis and the like.

The compounds of the invention are also indicated in the treatment of respiratory diseases, for example sarcoidosis, fibroid lung, idiopathic interstitial pneumonia and reversible obstructive airways disease which latter includes conditions such as asthma (e.g. bronchial asthma, allergic asthma, intrinsic asthma, extrinsic asthma and dust asthma), particularly chronic or inveterate asthma (e.g. late asthma and airway hyper-responsiveness), bronchitis and the like.

The compounds of the invention are also indicated in certain eye diseases such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' ophthalmopathy and the like.

The compounds of the invention are also indicated in the treatment of inflammation of mucosa and blood vessels such as gastric ulcers, vascular damage caused by ischemic diseases and thrombosis, ischemic bowel disease, inflammatory bowel disease, necrotizing enterocolitis, intestinal lesions associated with thermal burns and leukotriene B4-mediated diseases.

The compounds of the invention are also indicated in the treatment of renal diseases including interstitial nephritis, Goodpasture's syndrome, hemolytic-uremic syndrome and diabetic nephropathy; nervous diseases including multiple myositis, Guillain-Barré syndrome, Ménière's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases such as osteoporosis; skin diseases including dermatomyositis, leukoderma vulgaris, ichthyosis vulgaris, photoallergic sensitivity and cutaneous T-cell lymphoma; circulatory diseases selected from arteriosclerosis, atherosclerosis, aortitis syndrome, polyarteritis nodosa and myocardosis; collagen diseases including scleroderma, Wegener's granuloma and Sjogren's syndrome; adiposis; periodontal disease; nephrotic syndrome; hemolytic-uremic syndrome; and male pattern alopecia and alopecia senilis.

Further, the compounds of the invention are indicated in the treatment of diseases including intestinal inflammations/allergies such as Coeliac disease, proctitis, eosinophilic gastroenteritis, mastocytosis, Crohn's disease and ulcerative colitis; and food related allergic diseases which have symptomatic manifestation remote from the gasto-intestinal tract, for example migraine, rhinitis and eczema.

The compounds of the invention also have liver regenerating activity and/or activity in stimulating hypertrophy and hyperplasia of hepatocytes. Therefore, they are useful for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, non-A/non-B hepatitis and cirrhosis.

The compounds of the invention are also indicated for use as antimicrobial agents, and thus may be used in the treatment of diseases caused by pathogenic microorganisms and the like.

We therefore provide the use of a compound of the invention as a pharmaceutical.

Further, we provide the use of a compound of the invention in the manufacture of a medicament for use as an immunosuppressive agent.

For the above-mentioned therapeutic uses the dosage administered will, of course, vary with the compound employed, the mode of administration, the treatment desired (e.g. topical, parenteral or oral) and the disease indicated. However, in general, satisfactory results are obtained when the compounds are administered at a daily dosage of from 0.001 to 20 mg per kg of animal body weight.

For man the indicated total daily dosage is in the range of from 0.01 mg to 1000 mg and preferably from 0.5 mg to 100 mg, which may be administered, for example twice weekly, or in divided doses from 1 to 6 times a day or in sustained release form. Thus unit dosage forms suitable for administration, e.g. oesophageally, comprise from 0.01 mg to 500 mg, and preferably 0.5 mg to 100 mg of the compound preferably admixed with a solid or liquid pharmaceutically acceptable diluent, carrier or adjuvant.

According to our invention we also provide a pharmaceutical composition comprising preferably less than 80%, and more preferably less than 50% by weight, of a compound of the invention in combination with a pharmaceutically acceptable adjuvant, diluent or carrier. We also provide a process for the production of such a pharmaceutical composition which comprises mixing the ingredients. Examples of suitable adjuvants, diluents or carriers are: for tablets, capsules and dragees—microcrystalline cellulose, calcium phosphate, diatomaceous earth, a sugar such as lactose, dextrose or mannitol, talc, stearic acid, starch, sodium bicarbonate and/or gelatin; for suppositories—natural or hardened oils or waxes; and for inhalation compositions—coarse lactose. The compound of the invention is preferably in a form having a mass median diameter of from 0.01 to 10 μm. The compositions may also contain suitable preserving, stabilising and wetting agents, solubilisers (e.g. a water-soluble cellulose polymer such as hydroxypropyl methylcellulose, or a water-soluble glycol such as propylene glycol), sweetening and colouring agents and flavourings. The compositions may, if desired, be formulated in sustained release form.

For the treatment of reversible obstructive airways disease, we prefer the compound of the invention to be administered by inhalation to the lung, especially in the form of a powder.

According to a further aspect of the invention, there is provided a method of effecting immunosuppression which comprises administering a therapeutically effective amount of a compound of the invention to a patient.

The compounds of the invention have a number of chiral centres and may exist in a variety of stereoisomers. The invention provides all optical and stereoisomers, as well as racemic mixtures. The isomers may be resolved or separated by conventional techniques.

However, the preferred stereochemistry of various chiral carbon atoms are shown in formula Ia,

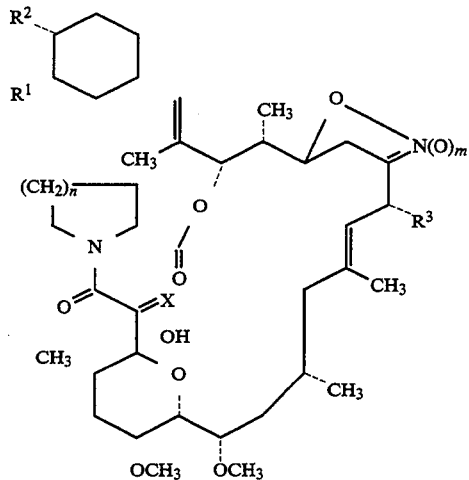

wherein $R^1$ to $R^3$, X, m and n are as first defined above.

When m is 0, we prefer C14 to have S-stereochemistry.

Test A

Mixed Lymphocyte Reaction (MLR) I

The MLR test was performed in microtitre plates, with each well containing $5 \times 10^5$ C57BL/6 responder cells (H-2$^b$), $5 \times 10^5$ mitomycin C treated (25 μg/ml mitomycin C at 37° C. for 30 minutes and washed three times with RPMI 1640 medium) BALB/C stimulator cells (H-2$^d$) in 0.2 ml RPMI 1640 medium supplemented with 10% fetal calf serum, 2 mM sodium hydrogen carbonate, penicillin (50 μg/ml) and streptomycin (50 μg/ml). The cells were incubated at 37° C. in a humidified atmosphere of 5% carbon dioxide and 95% of air for 68 hours and pulsed with $^3$H-thymidine (0.5 μCi) 4 hours before the cells were collected. The object compound of this invention was dissolved in ethanol and further diluted in RPMI 1640 medium and added to the cultures to give final concentrations of 0.1 μg/ml or less.

Test B

Mixed Lymphocyte Reaction (MLR) II

The MLR test was performed in 96-well microtitre plates with each well containing $3 \times 10^5$ cells from each of two responding donors in a final volume of 0.2 ml RPMI 1640 medium supplemented with 10% human serum, L-glutamine and penicillin/streptomycin. The compound under test was dissolved at 10 mg/ml in ethanol and further diluted in RPMI 1640. The cells were incubated at 37° C. in a humidified atmosphere at 5% carbon dioxide for 96 hours. 3H-thymidine (0.5 μCi) was added for the final 24 hours of the incubation to provide a measure of proliferation.

Test C

Graft versus Host Assay (GVH)

Spleen cells from DA and DAxLewis F1 hybrid rats were prepared at approximately $10^8$ cells/ml. 0.1 ml of these suspensions were injected into the rear footpads of DAxLewis F1 rats (left and right respectively). Recipient animals are dosed with the compound under test, either orally or subcutaneously, on days 0–4. The assay is terminated on day 7 when the popliteal lymph nodes of the animals are removed and weighed. The increase in weight of the left node relative to the weight of the right is a measure of the GVH response.

Test D

Inhibition of Interleukin-2 (IL-2) secretion

The test was performed following the method of S Sawada et al, J Immunol (6), Vol 139, pp1797–1803, but using the Jurkat cell line.

The invention is illustrated by the following Examples.

EXAMPLE b 1

(14R)-18-Allyl-1-hydroxy-12-[2-(4-hydroxy-3-methoxycyclo hexyl)-1-methylvinyl]-24,26-dimethoxy-13,20,22,28-tetramethyl-11,15,29-trioxa-4,16-diazatetracyclo [23.3.1.1$^{14,17}$.0$^{4,9}$]triaconta-16,19-diene-2,3,10-trione To a cold (5° C.), stirred solution of 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone C16 E-oxime (as prepared in Example 25, WO 89/05304, and separated from the Z-oxime by chromatography on silica) (250 mg) in dry dichloromethane (25 ml) under nitrogen was added Martin's sulfurane reagent portionwise until all the starting material had disappeared. The reaction mixture was then quenched with isopropanol (3 ml), and saturated aqueous sodium bicarbonate solution was added. The organic extract was then separated, dried (MgSO4), filtered and evaporated in vacuo to an oil. Chromatography on silica eluting with hexane in an increasing ethyl acetate gradient then gave the title compound as a foam (220 mg).

$^{13}$C NMR (CDCl$_3$) δ: 196.8 (C2); 169.4 (C10); 164.8 (C3); 160.6 (C17); 138 (C20); 125.6 (C19); 97 (C1); 83.3 (C14); 77.6 (C12); 75.5 (C24); 56.7 (C9); 48.4 (C21); 39.2 (C5); 28.7 (C8); 27 (C22); 24.7 (C6) MS (FAB): 886 [M+Rb]+; 784[M—OH]+

EXAMPLE 2

(14S)-18-Allyl-1-hydroxy-12-[2-(4-hydroxy-3-methoxycyclo hexyl)-1-methylvinyl]-24,26-dimethoxy-13,20,22,28-tetramethyl-11,15,29-trioxa-4,16-diazatetracyclo [23.3.1.1$^{14,17}$.0$^{4,9}$]triaconta-16,19-diene-2,3,10-trione To a cold (5° C.), stirred solution of 17-allyl-1,14-dihydroxy-12-[2-(4-hydroxy-3-methoxycyclohexyl)-1-methylvinyl]- 23,25-dimethoxy-13,19,21,27-tetramethyl-11,28-dioxa-4-azatricyclo[22.3.1.0$^{4,9}$]octacos-18-ene-2,3,10,16-tetraone C16 Z-oxime (as prepared in Example 25, WO 89/05304, and separated from the E-oxime by chromatography on silica) (260 mg) in dry dichloromethane (25ml) under nitrogen was added Martin's sulfurane reagent portionwise until all the starting material had disappeared. The reaction mixture was then quenched with isopropanol (3 ml), and saturated aqueous sodium bicarbonate solution was added. The organic extract was then separated, dried (MgSO4), filtered and evaporated in vacuo to an oil. Chromatography on silica eluting with hexane in an increasing ethyl acetate gradient then gave the title compound as a foam (230 mg).

$^{13}$C NMR (CDCl$_3$) δ: 194 (C2); 168.5 (C10); 165.6 (C3); 161.2 (C17); 138.2 (C20); 124.1 (C19); 97.3 (C1); 82 (C14); 78.4 (C12); 56.6 (C9); 52.1 (C21) MS (FAB): 886 [M+Rb]+; 824 [M+Na]+; 802 [M+H]+; 784 [M—OH]+

EXAMPLE 3

(14R)-1-Hydroxy-12-[2-(4-hydroxy-3-methoxycyclohexyl)-1-methylvinyl]-24,26-dimethoxy-18-ethyl-13,20,22,28-tetramethyl-11,15,29-trioxa-4,16-diazatetracyclo [23.3.1.1$^{14,17}$.0$^{4,9}$]triaconta-16,19-diene-2,3,10-trione a) 1,14-Dihydroxy-12-[2-(4-hydroxy-3-methoxycyclohexyl)-1-methylvinyl]-23,25-dimethoxy-17-ethyl-13,19,21,27-tetramethyl-11,28-dioxa-4-azatricyclo[22.3.1.0$^{4,9}$]octacos-18-ene-2,3,10,16-tetraone C16 oxime A solution of 1,14-dihydroxy-12-[2-(4-hydroxy-3-methoxycyclohexyl)-1-methylvinyl]-23,25-dimethoxy-17-ethyl-3,19,21,27-tetramethyl-11,28-dioxa-4-azatricyclo [22.3.1.0$^{4,9}$]octacos-18-ene-2,3,10,16-tetraone (FR-900520, EP 184162) (71 mg), hydroxylamine hydrochloride (80 mg) and pyridine (0.2 ml) in dry ethanol (5 ml) was refluxed under an atmosphere of nitrogen for 2 hours. The reaction mixture was then cooled and poured into a mixture of dilute aqueous hydrochloric acid (1N) and ethyl acetate. The ethyl acetate extract was washed with saturated aqueous sodium hydrogen carbonate solution, dried (MgSO4), filtered and evaporated in vacuo to an oil. Chromatograghy on silica eluting with hexane/acetone [2:1] then gave the Z-oxime (7 mg) followed by the E-oxime (10 mg).

MS (FAB): (E- and Z-oximes) 891 [M+Rb]+; 829 [M+Na]+; 807 [M+H]+; 789 [M—OH]+ $^{13}$C NMR (CDCl$_3$) δ:

E-oxime 197.1 (C2); 169.3 (C10); 165.3 (C3); 162 (C16); 138.1 (C19); 132.7 (C29); 128 (C31); 125.8 (C18); 97.3 (C1); 84.2 (C34); 39.7 (C13); 39.1 (C5); 24.3 (C8); 21.4 (C6); 21 (C7); 12 (C44); 9.9 (C39)

Z-oxime 169.5 (C2); 169 (C10); 165.3 (C3); 161.7 (C16); 138 (C19); 132.6 (C29); 128 (C31); 125.8 (C18); 97.3 (C1); 84.2 (C34); 9.5 (C39)

b) (14R)-1-Hydroxy-12-[2-(4-hydroxy-3-methoxycyclohexyl)-1-methylvinyl]-24,26-dimethoxy-18-ethyl-13,20,22,28-tetramethyl-11,15,29-trioxa-4,16-diazatetracyclo [23.3.1.1$^{14,17}$.0$^{4,9}$]triaconta-16,19-diene-2,3,10-trione To a cold (5° C.), stirred solution of a mixture of the E- and Z-oximes prepared following the method of step (a) (250 mg) in dry dichloromethane (25 ml) under nitrogen was added Martin's sulfurane reagent portionwise until all of the E-oxime had been consumed (as detected by thin layer chromatography). The reaction mixture was then quenched with isopropanol (3 ml), and saturated aqueous sodium bicarbonate solution was added. The organic extract was then separated, dried (MgSO4), filtered and evaporated in vacuo to an oil. Chromatography on silica eluting with hexane in an increasing ethyl acetate gradient then gave, in addition to the recovered Z-oxime (30 mg), the title compound as a foam (20 mg).

$^{13}$C NMR (CDCl$_3$) δ: 196.6 (C2); 169.3 (C10); 164.6 (C3); 160.8 (C17); 137.5 (C20); 126.1 (C19); 96.8 (C1); 82.9 (C14); 77.8 (C12); 75.4 (C24); 56.5 (C9); 48.3 (C21) MS (FAB): 874 [M+Rb]+; 772 [M—OH]+

EXAMPLE 4

(14S)-18-Allyl-1-hydroxy-12-[2-(4-hydroxy-3-methoxycyclo hexyl)-1-methylvinyl]-24,26-dimethoxy-13,20,22,28-tetra methyl-11,15,29-trioxa-4,16-diazatetracyclo[23.3.1.1$^{14,17}$.0$^{4,9}$]triaconta-16,19-diene-2,3,10-trione 16-N-oxide To a solution of 17-allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone C16-oxime (as prepared in Example 25, WO 89/05304) (0.5 g) in dry dichloromethane (20 ml) was added lead tetraacetate (0.32 g). After stirring for 5 minutes at room temperature, saturated aqueous sodium hydrogen carbonate solution was added and the reaction mixture was extracted with diethyl ether. The organic extract was washed with saturated aqueous sodium hydrogen carbonate solution, and this was dried (MgSO$_4$), filtered and evaporated to an oil in vacuo. Chromatography on silica eluting with hexane in an increasing acetone gradient then gave the title compound as a foam (220 mg).

$^{13}$C NMR (CDCl$_3$) δ: 196.7 (C2); 168.6 (C10); 166.4 (C3); 138.2 (C19); 134.9 (C41); 131.5 (C29); 128.4 (31); 119.1 (C18); 117.9 (C16); 116.9 (C42); 98.8 (C1); 83.9 (C34); 57.4 (C9); 48.1 (C20); 38.7 (C13); 38.5 (C5); 32.4 (C26); 31.1 (C36); 30.3 (C37); 27.8 (C21); 26.3 (C8); 24.3 (C6); 5.6 (C39) MS: 901.4 [M+Rb]$^+$; 839.7 [M+Na]$^+$; 817.7 [M+H]$^+$; 799.7 [M+H—H$_2$O]$^+$

EXAMPLE 5

The title compound of Example 1 was tested following the method of test A above, and the concentration required to inhibit the response by 50% (IC$_{50}$) was found to be $6 \times 10^{-10}$ M.

We claim:

1. A compound of formula I,

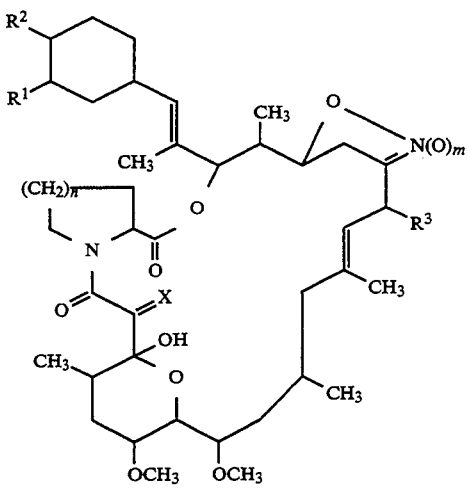

wherein
R$^1$ represents OH or OCH$_3$;
R$^2$ represents OH or H;
R$^3$ represents methyl, ethyl, propyl or allyl;
X represents O, (H,OH) or (H,H);
m represents 0 or 1;
n represents 1 or 2;
or a pharmaceutically acceptable derivative thereof; provided that when n is 1, then R$^3$ is allyl or propyl.

2. A compound according to claim 1, wherein R$^1$ represents OCH$_3$.

3. A compound according to claim 1 or claim 2, wherein R$^2$ represents OH.

4. A compound according to claim 1 or claim 2, wherein X represents 0.

5. A compound according to claim 1 or claim 2, wherein m represents 1.

6. A pharmaceutical composition comprising a compound of formula I, as defined in claim 1, or a pharmaceutically acceptable derivative thereof, in association with a pharmaceutically acceptable adjuvant, diluent or carrier.

7. A method of effecting immunosuppression which comprises administering a therapeutically effective amount of a compound of formula I, as defined in claim 1, or a pharmaceutically acceptable derivative thereof, to a patient.

* * * * *

UNITED STATES PATENT AND TRADEMARK OFFICE
CERTIFICATE OF CORRECTION

PATENT NO. : 5,384,316
DATED : January 24, 1995
INVENTOR(S) : Donald et al

It is certified that error appears in the above-indentified patent and that said Letters Patent is hereby corrected as shown below:

On the title page, item [54] and column 1, lines 2-4, delete the title and replace by --4,16-DIAZATETRACYCLO[23.3.1.1.$^{14,17}$.0$^{4,9}$]TRIACONTA-16,19-DIENE-2,3,10-TRIONE DERIVATIVES--.

Column 6, delete the formula Ia and replace by the following new formula Ia

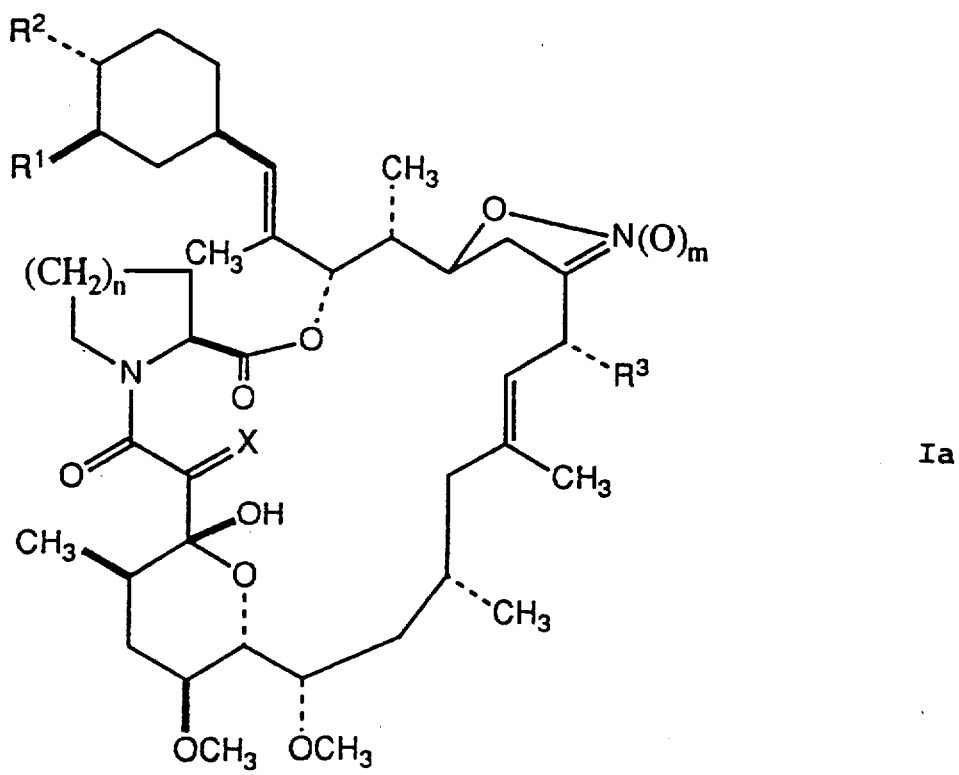

Ia

UNITED STATES PATENT AND TRADEMARK OFFICE
CERTIFICATE OF CORRECTION

PATENT NO. : 5,384,316
DATED : January 24, 1995
INVENTOR(S) : Donald et al

It is certified that error appears in the above-indentified patent and that said Letters Patent is hereby corrected as shown below:

Column 7 line 13, delete "EXAMPLE b1" and replace by
--EXAMPLE 1--.

Signed and Sealed this

Second Day of May, 1995

Attest:

BRUCE LEHMAN

Attesting Officer     Commissioner of Patents and Trademarks